United States Patent [19]

Häberle et al.

[11] Patent Number: 4,460,782
[45] Date of Patent: Jul. 17, 1984

[54] 2-ETHOXYMETHYL AND 2-METHOXYMETHYL N-(3,5-DICHLOROPHENYL) SUCCINAMIDES

[75] Inventors: Norman Häberle, Munich; Otto Eberle, Ottobrunn, both of Fed. Rep. of Germany

[73] Assignee: Consortium fur Elektrochemische Industrie GmbH, Munich, Fed. Rep. of Germany

[21] Appl. No.: 286,569

[22] Filed: Jul. 24, 1981

[30] Foreign Application Priority Data

Aug. 16, 1980 [DE] Fed. Rep. of Germany ....... 3030926

[51] Int. Cl.$^3$ .......................................... C07D 207/40
[52] U.S. Cl. ..................................... 548/547; 424/274
[58] Field of Search ............. 260/326.5 F, 326.5 FM; 548/544, 545, 547; 424/274

[56] References Cited

U.S. PATENT DOCUMENTS

| | | | |
|---|---|---|---|
| 3,184,475 | 5/1965 | Eby et al. | 260/326.5 FM |
| 3,586,697 | 6/1971 | Ozaki et al. | 260/326.5 FM |
| 3,741,981 | 6/1973 | Fujinami et al. | 260/326.5 FM |
| 3,745,170 | 7/1973 | Fujinami et al. | 548/544 |
| 3,804,856 | 4/1974 | Ooba et al. | 548/544 |
| 3,816,451 | 6/1974 | Crovetti et al. | 260/326.5 FM |

FOREIGN PATENT DOCUMENTS

| | | | |
|---|---|---|---|
| 0046274 | 12/1981 | European Pat. Off. | 548/544 |
| 2740848 | 3/1979 | Fed. Rep. of Germany | 260/326.5 FM |
| 2740845 | 3/1979 | German Democratic Rep. | 548/544 |
| 44-6272 | 3/1969 | Japan | 548/544 |

*Primary Examiner*—Paul M. Coughlan, Jr.
*Assistant Examiner*—David B. Springer
*Attorney, Agent, or Firm*—Collard, Roe & Galgano

[57] ABSTRACT

The invention relates to a selection of succinic acid imides that have, in the 2-position, alkoxy, alkoxyalkyl or acyloxy substituents having up to 4 carbon atoms and the imine components of which are derived from aliphatic amines having up to 5 carbon atoms or from aniline optionally having up to 2 substituents. The succinic acid imides according to the invention are used as fungicides. A method for their manufacture is also disclosed.

2 Claims, No Drawings

2-ETHOXYMETHYL AND 2-METHOXYMETHYL N-(3,5-DICHLOROPHENYL) SUCCINAMIDES

The invention relates to new substituted succinic acid imides, a process for their manufacture, and their use as fungicides.

Substituted succinic acid imides having herbicidal or fungicidal activity are already known. A comprehensive discussion on fungicidal succinic acid imides can be found in H. Büchel, "Pflanzenschutz und Schädlingsbekämpfung", 1977, Thieme-Verlag. Furthermore, according to European Patent No. 1,395, fungicidal succinic acid imides having, for example, cyclic alkenyl substituents are known. Moreover, Japanese Application Kokai No. 77/61,224, disclosed succinic acid imides having alkyl-thio-alkyl side chains and also exhibiting fungitoxic properties.

Succinic acid imides containing olefinic double bonds or chemically bonded sulphur are often, however, insufficiently stable chemically, especially in the field; they are subject to transposition reactions or, in the case of succinic acid derivatives containing sulphur, to oxidation and substitution reactions. The secondary products resulting therefrom are, however, not sufficiently active.

The object of the invention was to find succinic acid imides that, while having improved chemical stability and, therefore, a longer lasting action in the field, have a broad range of fungicidal action.

It has now been found that a selection of succinic acid imides having alkoxy, alkoxyalkyl or acyloxy substitution in the 2-position satisfy the above mentioned criteria.

The subject of the invention is therefore substituted succinic acid imides of the general formula

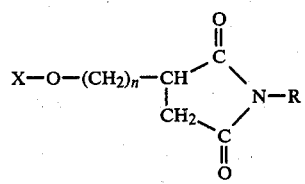

in which
n is 0 or 1
x represents an optionally branched alkyl radical having from 1 to 3 carbon atoms, or, provided that n is 0, an alkenyl radical having 3 carbon atoms, (or an acyl radical having from 2 to 4 carbon atoms) and represents an optionally branched alkyl radical having from 1 to 5 carbon atoms, an alkenyl radical having from 3 to 5 carbon atoms, or an optionally substituted phenyl radical having from 0 to 2 identical or different substituents selected from the group consisting of chlorine atoms, bromine atoms, and alkyl radicals and alkoxy radicals each having from 1 to 3 cabon atoms.

Preferred succinic acid imides according to the invention are those in which R represents the 3,5-dichlorophenyl radical.

A preferred process for the manufacture of the compounds according to the invention is characterized in that succinic acids, the acid chloride thereof or the anhydride thereof, that are substituted in the 2-position by an

in which
n is 0 or 1, and
X represents an optionally branched alkyl radical having from 1 to 3 carbon atoms, or, provided that n is 0, an alkenyl radical having 3 carbon atoms, or an acyl radical having from 2 to 4 carbon atoms, are reacted with amines of the general formula

in which
R represents an optionally branched alkyl radical having from 1 to 5 carbon atoms, an alkenyl radical having from 3 to 5 carbon atoms, or an optionally substituted phenyl radical having from 0 to 2 identical or different substituents selected from the group consisting of chlorine atoms, bromine atoms, and alkyl radicals and alkoxy radicals each having from 1 to 3 carbon atoms.

In this reaction, it is often advantageous to use water-binding or acid-binding agents, such as alkali metal carbonates or alkaline earth metal carbonates alkali, metal hydroxides or alkaline earth metal hydroxides or the analogous oxides, especially soda, potash, magnesia, or burnt, slaked or aerated lime.

In an especially advantageous process variant, the reaction of the succinic acid derivative with the corresponding amine is carried out in the presence of an inert solvent such as, for example, xylene and the water produced during the reaction is removed by azeotropic distillation. Tertiary amines, such as, inter alia, triethylamine or pyridine, accelerate the splitting off of water.

The substituted succinic acid derivatives required for the manufacture of the imides according to the invention can be obtained by basic known processes. Thus, alkoxysuccinic acids can be synthesized by the addition of alcohols to maleic acid esters or fumaric acid esters, it being advantageous in order to avoid transesterification and the addition of undesired alcohols to the double bond of the acids, to use, as starting materials, those esters, the alcohol moiety of which is also to be added to the double bond. The free acids can be obtained from the alkoxysuccinic acid esters by simple hydrolysis.

Alkoxyalkylsuccinic acid derivatives can be prepared by the addition of alcohols to itaconic acid esters. It is advantageous, in this case also, to use the same alcohol for esterification as is used for addition.

Acyloxysuccinic acid derivatives can be prepared by reacting malic acid with an excess of a carboxylic acid anhydride, the acyl radical of which is desired as substituent.

An excess of the carboxylic acid anhydride then brings about, in one reaction step, the formation of the anhydride of the acyloxysuccinic acids manufactured in that manner.

The manufacture of the amines to be used is likewise known. In general, the amines are commercially available. Examples of succinic acid derivatives, according to the invention, are:
2-methoxysuccinic acid N-(3-chlorophenyl)imide
2-methoxymethylsuccinic acid N-(3-chlorophenyl)imide
2-ethoxysuccinic acid N-(3-chlorophenyl)imide
2-ethoxymethylsuccinic acid N-(3-chlorophenyl)imide
2-propoxysuccinic acid N-(3-chlorophenyl)imide
2-isopropoxysuccinic acid N-(3-chlorophenyl)imide
2-allyloxysuccinic acid N-(3-chlorophenyl)imide 2-acetoxysuccinic acid N-(3-chlorophenyl)imide
2-propionyloxysuccinic acid N-(3-chlorophenyl)imide
2-methoxysuccinic acid N-(3,5-dichlorophenyl)imide
2-methoxymethylsuccinic acid N-(3,5-dichlorophenyl)imide
2-ethoxysuccinic acid N-(3,5-dichlorophenyl)imide
2-ethoxymethylsuccinic acid N-(3,5-dichlorophenyl)imide
2-propoxysuccinic acid N-(3,5-dichlorophenyl)imide
2-isopropoxysuccinic acid N-(3,5-dichlorophenyl)imide
2-allyloxysuccinic acid N-(3,5-dichlorophenyl)imide
2-acetoxysuccinic acid N-(3,5-dichlorophenyl)imide
2-propionyloxysuccinic acid N-(3,5-dichlorophenyl)imide
2-methoxysuccinic acid N-(2,6-dimethylphenyl)imide
2ethoxysuccinic acid N-(2,6-dimethylphenyl) imide
2ethoxymethylsuccinic acid N-(2,6-dimethylphenyl) imide
2-methoxymethylsuccinic acid N-(2,6-dimethylphenyl)imide
2-allyloxysuccinic acid N-(2,6-dimethylphenyl)imide
2-acetoxysuccinic acid N-(2,6-dimethylphenyl)imide
2-methoxysuccinic acid N-phenylimide
2-ethoxysuccinic acid N-phenylimide
2-acetoxysuccinic acid N-phenylimide
2-allyloxysuccinic acid N-phenylimide
2-methoxysuccinic acid N-(3-methoxyphenyl)imide
2-methoxymethylsuccinic acid N-(3-methoxyphenyl)imide
2-methoxysuccinic acid N-butylimide
2-methoxymethylsuccinic acid N-butylimide
2-methoxymethylsuccinic acid N-(but-2-yl)imide
2-ethoxysuccinic acid N-propylimide
2-methoxymethyl N-allylimide
2-isobutyroxysuccinic acid N-allylimide
2-methoxymethylsuccinic acid N-(3-bromophenyl)imide
2-ethoxysuccinic acid N-(3-bromophenyl)imide
2-isopropoxysuccinic acid N-(3-bromophenyl)imide The substituted succinic acid imides according to the invention, have fungitoxic properties. They are successful in controlling fungal diseases. They have been found, for example, to be highly effective against *Botrytis cinerea* (grey mold). Further examples are fungi such as types of *Alternaria, Septoria nodorum, Verticillium dahliae, Penicillium glaucum* and others. Furthermore, the active substances according to the invention can be used successfully against phytopathogenic fungi that adhere to the seeds, such as, for example, *Tilletia tritici* (wheat bunt), *Fusarium nivale* and types of *Helminthosporium*.

The fungicidal active substances according to the invention are suitable, without their field of use being limited thereto, for example, for use in viniculture, in grape cultivation, in strawberry cultivation and in horticulture, especially in salad crops or ornamental plants (cyclamens, geraniums, etc.). Use as a seed dressing has been found to be a further application, according to the invention.

The active substances according to the invention can be applied on their own or in admixture with other suitable plant-protecting agents. In general, however, they are used in admixture with solid or liquid diluents, or in solutions in solid or liquid solvents, containing from 0.01 to 95% by weight of active substances.

The mixtures or solutions are generally prepared in the form of emulsion concentrates, pastes, sprayable powders, granulates or micro-capsules.

Emulsion concentrates and pastes generally contain from 10% to 60% by weight, preferably from 15% to 40% by weight, of active substances, from 2% to 25% by weight of dispersing auxiliaries, and organic solvents and/or water.

Sprayable powders usually contain from 10% to 80% by weight, preferably from 15% to 70% by weight, of active substances, from 1% to 10% by weight of dispersing auxiliaries, and from 10% to 89% by weight of inert substances.

Granulates and dusting preparations contain, in addition to inert substances, binders and/or coating substances, from 1% to 10% by weight, preferably from 5% to 10% by weight, of active substance.

The following are used according to the invention:

(1) as dispersing auxiliaries, e.g.:
alkylsulphonates, arylsulphonates, methylcellulose, polymeric sulphonic acids and salts thereof, polyalcohols, fatty acid esters, fatty alcohol ethers and fatty amines;

(2) as organic solvents, e.g.:
alcohols, such as ethanol and butanols, dimethylformamide, dimethyl sulphoxide, N-methylpyrrolidone, and aromatic compounds, such as toluene and xylenes;

(3) as inert substances, e.g.:
kaolin, China clay, talc, calcium carbonate, highly disperse silica, silica gels, kieselguhr, diatomaceous earth, pumice, crushed maize, and thickening agents, such as starch and carboxymethylcellulose; and (4) as binders, e.g.:
magnesium sulphate, gypsum and gum arabic.

The fungicides according to the invention are formulated, for example, as follows:

(1) Emulsion concentrate:
20% by weight of active substances;
10% by weight of commercial ethoxylated anhydrosorbitol monolaurate (trademark "Tween Twenty"); and
70% by weight of dimethylformamide, (2) Sprayable powder:
20% by weight of active substance;
5% by weight of ammonium lignin sulphonate (trademark "Totanin");
10% by weight of sodium oleylmethyl tauride (trademark "Arkopon T Konz"); and
65% by weight of kaolin.

The application quantities of active substance may vary within wide ranges. When treating seeds, quantities of active substance of from 0.05 to 25 g/kg of seed are generally required.

The active substances according to the invention may be applied in any suitable form. There may be mentioned by way of example, pouring, syringing, spraying, dusting, coating and treating the seed (dressing).

The methods of preparing the succinic acids substituted according to the invention, and their fungicidal effectiveness, are illustrated below in the following Examples.

EXAMPLE 1

Preparation of 2-methoxysuccinic acid N-(3,5-dichlorophenyl) imide.

(a) 360.3 g of dimethyl fumarate (2.5 moles) are dissolved in 80 ml of methanol. A solution of sodium methoxide in methanol is then slowly added dropwise, while stirring. During this operation the temperature rises to 60° C. The solution is then heated under reflux for a further two hours, the methanol is distilled off, and the residue is dissolved in water. After acidification and extraction with ether, 422 g of crude product are obtained, from which a solid proportion (60 g of the starting material) is filtered off. The residue is distilled, and dimethyl 2-methoxysuccinate, having a boiling point of from 105° to 109° C. at 15 torr, is obtained in a 70.4% yield. After hydrolysis with 2N NaOH, the free 2-methoxysuccinic acid is obtained. The free acid is then converted, by heating for two hours with an excess of acetic anhydride, into 2-methoxysuccinic acid anhydride, with a 65% yield (b.p. at 14 torr from 120° to 123° C.).

(b) 130 g (1 mole) of 2-methoxysuccinic acid anhydride and 162 g (1 mole) of 3,5-dichloroaniline are heated under reflux for three hours, in 1500 ml of xylene. The resulting water is azeotropically separated off by means of a water separator. The xylene is then distilled off and the crude product is recrystallized from methanol/water. Melting point: 125° to 126° C.; yield: 75% of the theoretical yield.

EXAMPLE 2

Preparation of 2-methoxymethylsuccinic acid N-(3,5-dichlorophenyl)imide (a) 200 g of dimethyl itaconate are dissolved, together with 5.9 g of sodium methoxide, in 650 ml of methanol and the solution is left to stand for four days. The solution is then acidified with acetic acid and fractionally distilled. 240 g (83.4% of the theoretical yield) of dimethyl 2-methoxymethylsuccinate are obtained, at a boiling range of from 109° to 112° C. After the ester has been hydrolyzed with 2N HCl, the free acid is obtained in a yield of 80.3% of the theoretical yield.

Melting range: 94° to 98° C.

(b) 150 g of 2-methoxymethylsuccinic acid, 150g of 3,5-dichloroaniline and 0.5 g of triethylamine are heated under reflux, for four hours, in 1.5 liters of xylene, and the water formed is separated off by means of a water separator. The solvent is then drawn off. 250 g of end product are obtained in crystalline form.

Melting point: 95°–98° C.; boiling point at 0.1 torr: 155° to 157° C.

EXAMPLE 3

Preparation of 2-acetoxysuccinic acid N-(3,5-dichlorophenyl) imide (a) 250 g (1.86 mole) of malic acid are dissolved in 500 ml of acetic anhydride and a further 1 ml of concentrated sulphuric acid is added thereto. The mixture is then heated at 140° C. for four hours. Finally, it is concentrated in vacuo and the residue is fractionally distilled. 2-acetoxysuccinic acid anhydride is obtained in a 60% yield. Boiling point at 0.01 torr: 108° to 113° C.; melting point: 56° C.

(b) 158 g (1 mole) of 2-acetoxysuccinic acid anhydride and 162 g (1 mole) of 3,5-dichloroaniline are heated under reflux for three hours, in 1 liter of xylene. The resulting water is azeotropically separated off by means of a water separator. The xylene is then distilled off and the crude product is recrystallized from ethyl acetate. The yield of end product is 70.3% of the theoretical yield.

Melting point: 107° C.

EXAMPLE 4

Grape juice test 20 ml of a nutrient solution consisting of grape juice and distilled water in a weight ratio of 1:1 are poured into glass petri dishes and the active substances listed in Table 1 are added thereto in the concentrations indicated. Each test mixture is then inoculated with 50 µl of a suspension of *Botrytis* spores, prepared by washing the *Botrytis* spores from an agar culture with distilled water.

After incubation periods of 10 and 20 days, respectively, at 20° C., the extent of fungal development on the surface of the nutrient solution is assessed.

The effectiveness is calculated as a percentage, according to the following formula:

$$\frac{100 - \text{fungal growth, treated}}{\text{fungal growth, untreated}} \times 100$$

TABLE 1

Effectiveness against *Botrytis cinerea* in the grape juice test at 10 ppm active substance concentration

| Active substance | % effectiveness after 10 days | % effectiveness after 20 days |
|---|---|---|
| 2-methoxysuccinic acid N—(3,5-dichlorophenyl)imide | 100 | 100 |
| 2-ethoxysuccinic acid N—(3,5-dichlorophenyl)imide | 100 | 100 |
| 2-isopropoxysuccinic acid N—(3,5-dichlorophenyl)imide | 100 | 100 |
| 2-allyloxysuccinic acid N—(3,5-dichlorophenyl)imide | 80 | 80 |
| 2-methoxymethylsuccinic acid N—(3-chlorophenyl)imide | 90 | 80 |
| 2-methoxymethylsuccinic acid N—(3,5-dichlorophenyl)imide | 100 | 100 |
| 2-acetoxysuccinic acid N—(3,5-dichlorophenyl)imide | 80 | 70 |

COMPARISON EXAMPLE 1

The test set-up and procedure are the same as those described in Example 4.

TABLE 2

Effectiveness against *Botrytis cinerea* in the grape juice test at 10 ppm active substance concentration

| Active substance | % effectiveness after 10 days | % effectiveness after 20 days |
|---|---|---|
| 2-(cyclohex-2-en-1-yl)-succinic acid N—(3,5-dichlorophenyl)imide | 0 | 0 |
| 2-(pent-2-en-1-ylmercapto)-succinic acid N—(3,5-dichlorophenyl)imide | 80 | 45 |

The comparison substances differ from the active substances according to the invention, in the substituents in the 2-position. In the one case, the oxygen function is lacking, and, in the other, it is replaced analogously by chemically bonded sulphur.

Comparison of the results, according to Table 1 with those of Table 2, reveals the high effectiveness of the active substances according to the invention and their lasting action, as compared with the comparison substances. It also becomes especially clear that the action of preparations containing sulphur, decreases considerably after 20 days.

EXAMPLE 5

Spore germination test

50 μl of a solution or suspension containing 500 ppm of the active substance are introduced into the hollow of hollow-ground slides, together with 50 μl of a spore suspension prepared by washing the spores from an agar culture with a nutrient solution containing, per liter, 10 g of sugar, 1 g of glycol, 1 g of $KH_2PO_4$ and 0.5 g of $MgSO_4$.

The slides are kept at 20° C. for 48 hours in a petri dish, the base of which is covered with a moistened filter paper.

The ratio of germinated and ungerminated spores is then compared with an untreated control sample.

The effectiveness is calculated as a percentage according to the following formula:

$$\frac{100 - \text{number of germinated spores, treated}}{\text{number of germinated spores, untreated}} \times 100$$

The results are summarized in Table 3:

TABLE 3

Fungitoxicity of active substances according to the invention against fungi spore at 500 ppm active substance concentration

| Active substance | Alternaria solani | Botrytis cinerea | Fusarium nivale | Penicillium glaucum | Septoria nodorum |
|---|---|---|---|---|---|
| 2-methoxysuccinic acid N—(3,5-dichlorphenyl)imide | 90 | 100 | 90 | 80 | — |
| 2-ethoxysuccinic acid N—(3,5-dichlorphenyl)imide | 70 | 100 | 80 | 80 | — |
| 2-isopropoxysuccinic acid N—(3,5-dichlorphenyl)imide | 70 | 100 | 50 | 100 | 50 |
| 2-allyloxysuccinic acid N—(3,5-dichlorphenyl)imide | 80 | 100 | 70 | 80 | 80 |
| 2-methoxymethylsuccinic acid N—(3,5-dichlorphenyl)imide | 100 | 100 | 100 | 100 | 70 |
| 2-acetoxysuccinic acid N—(3,5-dichlorphenyl)imide | 100 | 100 | 100 | 100 | 70 |

COMPARISON EXAMPLE

The test set-up and procedure are the same as those described in Example 5. The results are shown in Table 4.

TABLE 4

Fungitoxicity of comparison active substances against fungi spore at 500 ppm active substance concentration

| Active substance | Alternaria solani | Botrytis cinerea | Fusarium nivale | Pencillium glaucum | Septoria nodorum |
|---|---|---|---|---|---|
| 2-(cyclohex-2-en-1-yl)-succinic acid N—(3,5-dichlorophenyl)imide | 30 | 25 | 0 | 0 | 30 |
| 3-(3,5-dichlorophenyl)-1-isoproylcarbamoyl-hydantoin Trademark: "Rovral" | 0 | 100 | 0 | 60 | 30 |
| 2-(pent-2-en-1-ylmercapto)-succinic acid N—(3,5-dichlorophenyl)imide | 20 | 20 | 20 | 10 | 10 |

The results from Example 5 and Comparison Example 2 illustrate the broader range of action of the compounds according to the invention, as compared with the comparison preparations. This property is often of decisive importance: for example, attendant fungi such as *Alternaria solani* and *Penicillium glaucum* often occur together with *Botrytis cinerea*. If a fungicide is directed at only one particular strain of fungus, increased growth of the types of attendant fungus will often be observed. Accordingly, an adequate treatment of a fungal disease is ensured only if the fungicide used has such a broad range of action that it controls the greater complex of the fungal disease.

EXAMPLE 6

Seed dressing test

Healthy wheat seed is uniformly infected with spores of *Tilletia tritici*. The infected seed is subsequently dressed carefully with the active substances according to the invention, prepared in the form of dry dressings.

After being dressed, the wheat grains are placed in dishes of damp earth. Incubation takes place in a drying cupboard at from 14° to 17° C. After 48 hours, the spores adhering to the grains are removed by pressing the grains into loam/earth.

After incubation for a further eight days at from 14° to 17° C. in the drying cupboard, the ratio of germinated and ungerminated spores as, compared with an untreated control, is determined under a binocular microscope.

The action of the active substances according to the invention, is given as percentage germination inhibition.

TABLE 5

Dressing test against wheat bunt (*Tilletia tritici*)

| Active substance | % effectiveness at 100 ppm active substance concentration |
|---|---|
| 2-methoxysuccinic acid N—(3,5-dichlorophenyl)imide | 95 |
| 2-methoxysuccinic acid N—(4-propylphenyl)imide | 80 |
| 2-ethoxysuccinic acid N—(3,5-dichlorophenyl)imide | 90 |
| 2-isopropoxysuccinic acid N—(3,5-dichlorophenyl)imide | 100 |
| 2-allyloxysuccinic acid | 100 |

TABLE 5-continued

Dressing test against wheat bunt (*Tilletia tritici*)

| Active substance | % effectiveness at 100 ppm active substance concentration |
|---|---|
| N—(3,5-dichlorophenyl)imide 2-methoxymethylsuccinic acid | 80 |
| N—(3-chlorophenyl)imide 2-methoxymethylsuccinic acid | 100 |
| N—(3,5-dichlorophenyl)imide 2-methoxymethylsuccinic acid | 80 |
| N—(but-2-yl)imide 2-acetoxysuccinic acid | 100 |
| N—(3,5-dichlorophenyl)imide 2-isobutyroxysuccinic acid | 80 |
| N—allylimide | |

COMPARISON EXAMPLE 3

The test set-up and procedure are the same as those described in Example 6.

The results are shown in Table 6.

TABLE 6

Dressing test against wheat bunt (*Tilletia tritici*)

| Active substance | % effectiveness at 100 ppm active substance concentration |
|---|---|
| 2-(cyclohex-2-en-1-yl)-succinic acid N—(3,5-dichlorophenyl)imide | 0 |
| 3-(3,5-dichlorophenyl)-1-isopropylcarbymoylhydantoin Trademark: "Rovral" | 75 |
| 2-(pent-2-en-1-ylmercapto)-succinic acid N—(3,5-dichlorophenyl)imide | 40 |

Comparison of the results according to Example 6 and Comparison Example 3, show again the superior fungicidal effectiveness of the succinic acid derivatives, according to the invention, as compared with the comparison preparations.

While several embodiments and examples of the present invention have been shown and described, it will be obvious to those skilled in the art that other changes and variations can be made in carrying out the present invention, without departing from the spirit and scope thereof, as defined in the appended claims.

What is claimed is:

1. 2-methoxymethylsuccinic acid N-(3,5-dichlorophenyl)imide.
2. 2-Ethoxymethylsuccinic acid N-(3,5-dichlorophenyl)imide.

* * * * *